US009662066B2

(12) United States Patent
Ledet et al.

(10) Patent No.: US 9,662,066 B2
(45) Date of Patent: May 30, 2017

(54) SENSOR SYSTEM, IMPLANTABLE SENSOR AND METHOD FOR REMOTE SENSING OF A STIMULUS IN VIVO

(71) Applicant: IO SURGICAL, LLC, Schenectady, NY (US)

(72) Inventors: Eric Howard Ledet, Schenectady, NY (US); Rebecca Ann Wachs, Albany, NY (US); Keegan Paul Cole, Windham, NH (US); David Fiorella, Arlington, VA (US)

(73) Assignee: IO Surgical, LLC, Schenectady, NY (US)

( * ) Notice: Subject to any disclaimer, the term of this patent is extended or adjusted under 35 U.S.C. 154(b) by 0 days.

(21) Appl. No.: 14/375,175

(22) PCT Filed: Feb. 5, 2013

(86) PCT No.: PCT/US2013/024706
§ 371 (c)(1),
(2) Date: Jul. 29, 2014

(87) PCT Pub. No.: WO2013/119528
PCT Pub. Date: Aug. 15, 2013

(65) Prior Publication Data
US 2014/0378783 A1    Dec. 25, 2014

Related U.S. Application Data

(60) Provisional application No. 61/633,225, filed on Feb. 7, 2012, provisional application No. 61/688,898, filed on May 24, 2012.

(51) Int. Cl.
*A61B 5/00*    (2006.01)
*A61B 5/03*    (2006.01)
(Continued)

(52) U.S. Cl.
CPC .......... *A61B 5/4851* (2013.01); *A61B 5/0002* (2013.01); *A61B 5/0031* (2013.01);
(Continued)

(58) Field of Classification Search
CPC ....... A61B 5/0002; A61B 5/0031; A61B 5/03; A61B 5/07; A61B 5/6846; A61B 3/16;
(Continued)

(56) References Cited

U.S. PATENT DOCUMENTS 4,127,110 A * 11/1978 Bullara ................ A61B 5/0002
128/903
5,005,577 A * 4/1991 Frenkel .................... A61B 3/16
600/398

(Continued)

FOREIGN PATENT DOCUMENTS

WO        01-12092 A1     2/2001
WO        03/061467 A1    7/2003
WO      2009/146090 A1   12/2009

OTHER PUBLICATIONS

Collins, C. C. "Miniature Passive Pressure Transensor for implanting in the Eye"; IEE Transactions on Bio-Medical Engineering, vol. BME 1-4; No. 2; (Apr. 1967); p. 74-83.*

(Continued)

*Primary Examiner* — William Thomson
*Assistant Examiner* — Marie Archer
(74) *Attorney, Agent, or Firm* — Heslin Rothenberg Farley & Mesiti P.C.

(57) ABSTRACT

A sensor system for sensing a stimulus in vivo includes an implantable sensor. The sensor comprises a passive resonator circuit having a resonant frequency and including at least a pair of generally parallel spirally wound unconnected conductive coils sandwiching a layer of solid dielectric material that manifest a change in property affecting the resonant frequency in response to application of the stimulus to the layer. A resonant frequency of the sensor is modulated by altering the spacing or gap between the coils or altering the overlapping area of the coils. The sensor is energized through application of radiofrequency energy and the (Continued)

responding resonant frequency is detected. The sensor can be advantageously attached to a medical implant to form a practical smart implant for clinical purposes.

39 Claims, 12 Drawing Sheets (51) Int. Cl.
*H01F 5/06* (2006.01)
*H01F 5/00* (2006.01)
*A61B 5/01* (2006.01)
*A61B 5/053* (2006.01)
*A61B 5/103* (2006.01)
*A61B 5/145* (2006.01)

(52) U.S. Cl.
CPC .................. *A61B 5/01* (2013.01); *A61B 5/03* (2013.01); *A61B 5/053* (2013.01); *A61B 5/1036* (2013.01); *A61B 5/14539* (2013.01); *A61B 5/14546* (2013.01); *A61B 5/4504* (2013.01); *A61B 5/686* (2013.01); *H01F 5/003* (2013.01); *H01F 5/06* (2013.01)

(58) Field of Classification Search
CPC ....... A61B 2560/0219; A61B 2562/028; A61F 9/0017; H01F 5/003; H01F 5/06
See application file for complete search history.

(56) References Cited

U.S. PATENT DOCUMENTS

| | | |
|---|---|---|
| 6,025,725 A | 2/2000 | Gershenfeld et al. |
| 6,111,520 A | 8/2000 | Allen et al. |
| 6,544,193 B2* | 4/2003 | Abreu .................. A61B 3/1241 600/558 |
| 6,667,725 B1 | 12/2003 | Simons et al. |
| 6,939,299 B1 | 9/2005 | Petersen et al. |
| 7,191,013 B1* | 3/2007 | Miranda ............... A61B 5/0031 607/60 |
| 2001/0016683 A1 | 8/2001 | Darrow et al. |
| 2004/0082867 A1 | 4/2004 | Esch et al. |
| 2009/0299228 A1* | 12/2009 | Lozier ................ A61B 17/7275 600/587 |
| 2011/0152725 A1* | 6/2011 | Demir .................. A61B 5/0031 600/587 |
| 2011/0282175 A1 | 11/2011 | Geissler et al. |

OTHER PUBLICATIONS

Jow, U-E. "Modeling and Optimization of Printed Spiral Coils in Air, Saline, and Muscle Tissue Environments"; IEE Transactions on Biomedical Circuits and Systems; vol. 3; No. 5, Oct. 2009; p. 339-347.*
Wachs, R. A. et al; "Elementary Implantable Force Sensor: For Smart Orthopaedic Implants"; Adv Biosens Bioelectron. Dec. 2013; 2(4). p. 1-14.*
Ashoori, E. et al; "Design of Double Layer Printed Spiral Coils for Wirelessly-Powered Biomedical Implants"; 33rd Annual International Conference of the IEEE EMBS Boston, Massachusetts USA, Aug. 30-Sep. 3, 2011; p. 2882-2885.*
Melik, R. et al; "Bio-implantable passive on-chip RF-MEMS strain sensing resonators for orthopaedic applications"; J. Micromech. Microeng. 18 (2008) 115017 (9pp).*
Rosengren, L. et al.; "A system for passive implantable pressure sensors"; Sensors and Actuators A, 43 (1994) 55-58.*
International Search Report for International Application No. PCT/US2013/024706, dated May 28, 2013.

* cited by examiner

SENSOR SYSTEM, IMPLANTABLE SENSOR AND METHOD FOR REMOTE SENSING OF A STIMULUS IN VIVO

FIELD OF THE INVENTION

This invention relates generally to a sensor system for remotely sensing a stimulus and, more particularly, to a sensor system employing an implantable sensor especially well suited for in vivo clinical applications.

BACKGROUND ART

Personalized medicine improves outcomes and reduces costs by enabling more accurate diagnoses and more optimal treatments. Patients are back to health and back to work more quickly, thus reducing the impact on an individual's life and the overall economic burden of disease.

In orthopedic and neurological surgery, intervention often results in placement of a permanent implant. On a patient-specific basis, the implant's physical environment potentially provides a wealth of diagnostic data regarding the progression of healing and prognosis of an outcome. Earlier detection of failure fosters earlier revision. Earlier diagnosis of healing fosters earlier return to work. In this way, the clinical utility of smart implants in musculoskeletal disease is vast. There are clinical indications in many areas of clinical medicine which are opportunities for smart implant-based diagnosis, intra-operative monitoring and personalized post-operative care to reduce the burden of the disease.

For musculoskeletal diseases, implants are an opportune vehicle for facilitating personalized medicine. "Smart implants" can be used to house implantable sensors that measure the local physical environment and provide quantitative real time patient-specific data that cannot be obtained any other way. Such data can be provided to the caregiver or directly to the patient to facilitate accurate diagnoses, guide treatments, and optimized rehabilitation and therapy.

Since the 1960's, the clinical value of implantable sensors in orthopedic and neurological surgery has been demonstrated in the research literature. Yet, for the last 45 years, the technology has not been translated into clinical practice. Implantable systems for research have been too bulky, too expensive, prone to failure due to complexity, and have necessitated surgical modification to the clinical implants which act as vehicles to carry sensors into the body. This has relegated implantable sensors to pre-clinical studies and very small patient populations in research studies. For smart implants to become part of clinical practice, the sensors must be robust, inexpensive, and compatible with off-the-shelf implants.

BRIEF SUMMARY OF THE INVENTION

To translate implantable sensing into clinical practice, the present invention provides a sensor system for sensing a stimulus in vivo including an implantable sensor comprising a passive resonator circuit having a resonant frequency and including at least a pair of generally parallel spirally wound unconnected conductive coils sandwiching a layer of solid dielectric material that manifests a change in property affecting the resonant frequency in response to application of the stimulus to the layer. The resonant frequency of the simple implantable sensor is read wirelessly using an external radiofrequency (R.F.) antenna. The external antenna both energizes the system and senses the resonant frequency. The resonant frequency is modulated by the stimulus of interest.

The sensors can be tuned, e.g. by appropriate selection of the dielectric material, to be sensitive to physical parameters such as force, absolute pressure, or temperature, to measure proximity or relative motion, or to measure specific pathogens, such as bacteria to detect infection.

The new sensor system is fundamentally different from previous systems used in orthopedic applications. The sensor is extremely simple employing only a pair of flat parallel coils, each behaving as both an inductor and a capacitor. There is no battery. There is no telemetry. There are no electrical connections. Because the system is so simple, it is also extremely inexpensive (both materials and fabrication). It is also robust because there are no electrical connections to fail. Significantly, because of its small size, there is little or no modification required of the host implant. To our knowledge, Applicants are the first to adapt and implement this genre of sensor to clinical applications.

There are multiple clinical applications for this invention, e.g., in orthopedics and neurosurgery: (i) monitoring of fracture healing and early detection of non-union; (ii) monitoring spine fusion and early detection of pseudarthrosis following spinal arthrodesis; (iii) intra-and post-operative measurement of force balance in the knee for arthroplasty; (iv) early detection of osteolysis and implant loosening following total hip arthroplasty; and (v) early detection of local infection around an implant.

The sensor and sensor system of the present invention may also be advantageously employed in other clinical and medical applications, for example, vascular, cardiac, gastrointestinal, etc., and non-medical applications, such as monitoring pressure in a pipe, or other stimuli or parameters in remote, hostile, or inaccessible environments.

In one aspect of the present invention, a sensor system for sensing a stimulus in vivo is provided. The sensor system includes a sensor implantable in a patient. The sensor includes at least a first single component L-C element, a second single component L-C element spaced from and electrically unconnected to the first element, and a solid dielectric layer sandwiched between the first element and the second element. The solid dielectric layer has a property that varies in response to application of the stimulus to the solid dielectric layer. The system further includes an energizer, external to the patient, energizing the first element and the second element with radiofrequency energy such that the energized first element and second element form a passive resonator circuit having a resonant frequency that varies with the property. A detector, also external to the patient, determines the resonant frequency of the passive resonator circuit as a measure of the stimulus applied to the dielectric layer in vivo.

The stimulus to be sensed may be force, load, strain, shear, temperature, absolute pressure, displacement, pH, deformation, a chemical marker and/or a biomarker.

The variable property of the solid dielectric layer may comprise surface deformation, surface displacement, layer dimension, layer size, layer shape, layer volume, capacitance and/or inductance.

The sensor is preferably devoid of an enclosure and readily attachable to a medical implant without modifying geometry of the implant. Preferably, the first element comprises a first flat spiral shaped conductive coil wound clockwise, and the second element comprises a second flat spiral shaped conductive coil wound counterclockwise.

The sensor system may include at least one additional sensor providing multi-axial sensing of the stimulus and/or concurrent sensing of multiple stimuli.

The energizer and the detector of the sensor system may be combined, and, advantageously, may comprise a grid dip oscillator and an antenna.

In another aspect, the present invention provides a method of sensing a stimulus in vivo. The method includes: selecting a solid dielectric material that manifests a change in property in response to application of the stimulus to the solid dielectric material; implanting, in a position in a patient subject to the stimulus, a passive resonator circuit having a resonant frequency and comprising at least a pair of generally parallel spirally wound unconnected conductive coils sandwiching a layer of the solid dielectric material, stimulus produced variations in the property affecting the resonant frequency; energizing the passive resonator circuit with radiofrequency energy from a source external to the patient; remotely detecting the resonant frequency of the energized passive resonator circuit, and determining a value of the stimulus applied to the layer of dielectric material in vivo from the detected resonant frequency.

The implanting step of the method preferably comprises attaching the passive resonator circuit to a medical implant. The determined value of the stimulus may be used for: determining progression of healing, outcome prognosis, detection of implant failure, intra-operative monitoring, and/or personalized post-operative care.

In a further aspect, the present invention provides a sensor for sensing a stimulus. The sensor includes a passive resonator circuit having a resonant frequency and including at least a pair of generally parallel spirally wound unconnected conductive coils sandwiching a layer of solid dielectric material that manifests a change in property affecting the resonant frequency in response to application of the stimulus to the layer.

Preferably, the passive resonator circuit is un-encapsulated, adapted to operate in an aqueous environment, and is remotely energized, batteryless and telemetryless.

Also, preferably, a first coil of the pair is wound clockwise and a second coil of the pair is wound counterclockwise.

The first coil and the second coil are, preferably, flat, substantially parallel to each other and disposed on opposite sides of the solid dielectric layer. The first and second coils may either be simply stacked adjacent to, or adhered to, respective opposite surfaces of the solid dielectric layer.

The first and second coils may comprise insulated wires wound concentrically that maintain their respective shape after being wound. The windings of each coil may be bonded together to maintain their respective shape. The sensor may further include a substrate to maintain the shape of the wound coil. The substrate may comprise an epoxy, a polymer, an elastomer, a ceramic, a composite material and/or a rigid support material.

Each coil preferably comprises a conductor wound concentrically and continuously around itself from a central point outward with an insulator between windings.

Advantageously, at least one coil of the sensor may be a micro machined or a micro fabricated part.

The sensor is advantageously employed in combination with an energizer energizing the passive resonator circuit with radiofrequency energy and a detector determining a resonant frequency of the passive resonator circuit as a measure of the stimulus applied to the layer of solid dielectric material.

The passive resonator circuit of the sensor may advantageously be composed of biocompatible material and adapted for implantation in a patient for sensing the stimulus in vivo. This sensor may be attached to a medical implant to form a smart implant.

BRIEF DESCRIPTION OF THE DRAWING FIGURES

These and other aspects of the present invention will be more fully understood from the following detailed description, read in conjunction with the accompanying drawings, in which.

DETAILED DESCRIPTION

Figure 1:
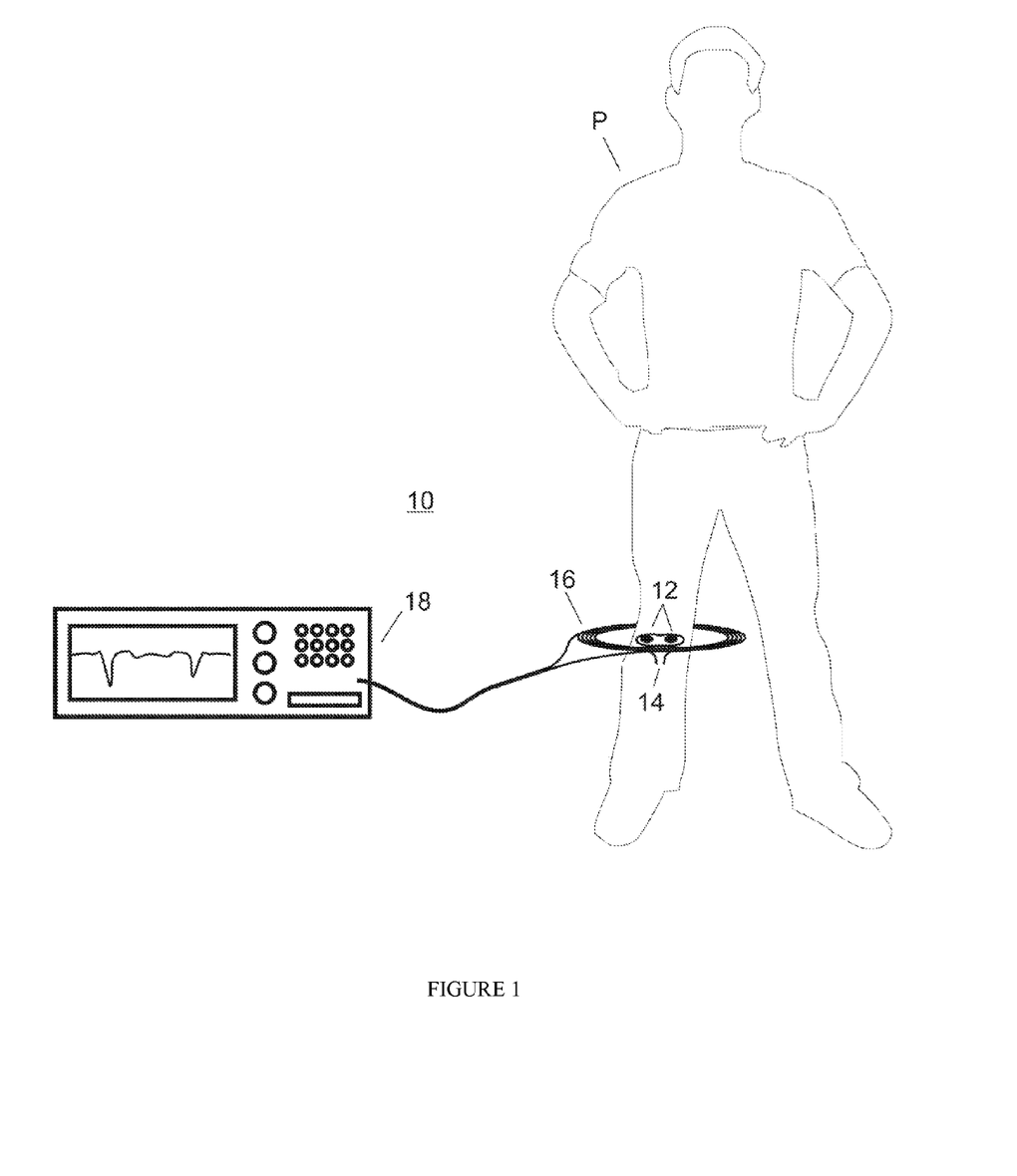
FIG. 1 depicts a sensor system of the present invention.

As illustrated in FIG. 1, the sensor system 10 of the present invention may employ an implantable sensor 12 attached to a medical implant 14 to sense a stimulus in a patient P. As more fully discussed below, the sensor 10 may comprise a passive resonator circuit of unique design. The sensor of this "smart implant" is wirelessly energized by a remote energizer 16 preferably associated with a resonant frequency detector 18.

The sensor system 10 may be used for measurement of displacement, deformation, strain, shear, force, load, absolute pressure, temperature, pH, or other physical, chemical or biological stimulus or parameter.

In simple form, a passive resonator circuit is comprised of two electrical components, a capacitor (C) and an inductor (L). When the two component L-C circuit is excited with radiofrequency (RF) energy, it resonates. The resonant frequency is a function of both the inductance and the capacitance. When either one changes, the resonant frequency is modulated.

The resonant frequency of the implantable passive resonator circuit 13 can easily be measured wirelessly via an external antenna using a grid dip oscillator which serves as both the energizer 16 and detector 18 of the sensor system. The oscillator generates RF energy and sweeps a range of frequencies around the resonant frequency of the sensor. The RF energy causes the sensor to resonate. At its resonant frequency, the sensor absorbs energy which is observed as a "dip" on the oscillator. If the resonant frequency of the sensor changes, the dip will move accordingly. In this way, changes in the resonant frequency of the sensor can be read dynamically. Other techniques and equipment may also be used to determine the resonant frequency.

Through a simple design, an L-C circuit can, for example, function as a passive, stand-alone force sensor. Physically, two coils of electrical conductors in close proximity to each other form an inductor. Similarly, two flat parallel conductive plates separated by a thin layer of dielectric material form a capacitor. If the distance between the two plates of the capacitor changes, the capacitance is modulated and the resonant frequency changes accordingly. Applying a force to the capacitor will cause the dielectric layer between the plates to deform which reduces the gap between the plates which modulates capacitance and alters the resonant frequency. In this way, a simple L-C circuit can function as a force sensor.

In accordance with the present invention, the passive resonator circuit is further simplified by employing a pair of unconnected single component L-C elements sandwiching a layer of solid dielectric material. The inductor and capacitor components of the standard L-C circuit are combined into a single flat spirally wound conductive coil. A pair of such coils, preferably wound in opposite directions, and disposed in parallel and concentrically aligned on opposite sides of the layer of solid dielectric material form the implantable sensor of the present invention.

Figure 2:
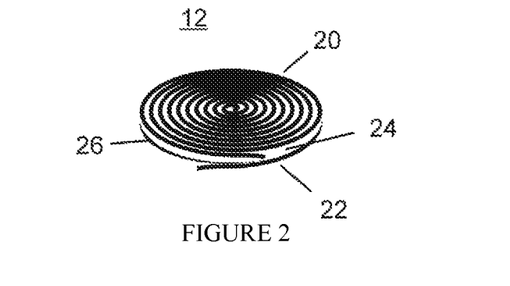
FIG. 2 is an enlarged perspective view of a bonded sensor of the current invention.
Figure 2A:
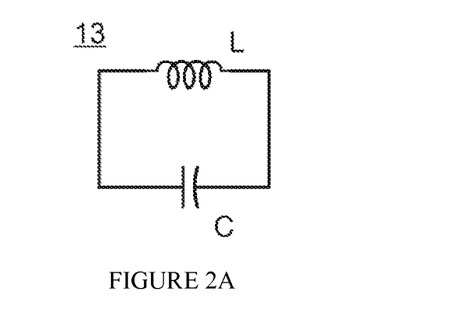
FIG. 2A depicts the passive resonator circuit formed by the energized sensor of the present invention.
Figure 3:
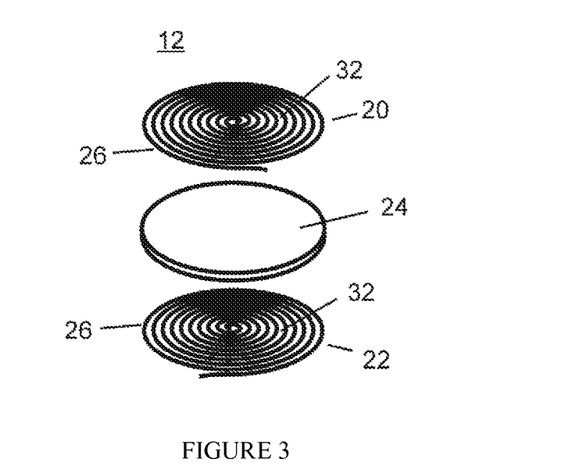
FIG. 3 is an exploded view of the sensor of FIG. 2.
Figure 4:
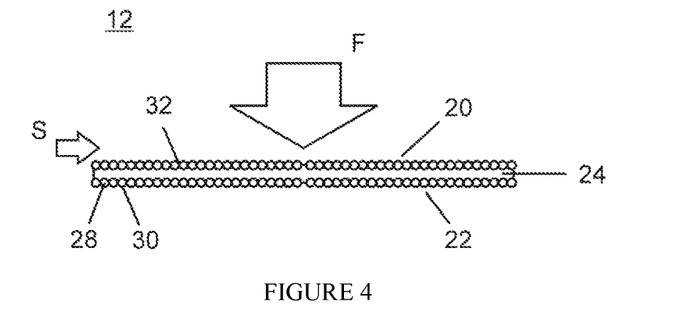
FIG. 4 is a cross-sectional view of the sensor of FIG. 2.

FIGS. 2-4 depict a first embodiment of the implantable sensor 12 of the present invention. The sensor comprises a passive resonator circuit 13, diagrammatically depicted in FIG. 2A, having a resonant frequency and includes at least a pair of generally parallel, flat, spirally wound unconnected conductive coils 20, 22 sandwiching a layer 24 of solid dielectric material that manifests a change in property affecting the resonant frequency in response to application of the stimulus to the layer. The stimulus may, for example, be an axial force, represented by the arrow F in FIG. 4, resulting in a decrease in spacing between coils 20, 22, or shear, represented by the arrow S in FIG. 4, altering overlapping areas of the coils. In the version of FIG. 2, the coils 20, 22 are adhered to opposite faces of the layer of solid dielectric material by a suitable adhesive 26, such as a biocompatible polymer, elastomer, or composite; cyanoacrylate being presently preferred. The coils are substantially concentric but preferably wound in opposite directions, i.e., one is wound clockwise while the other is wound counterclockwise. The shape of the windings of each coil may be generally circular, oval, square, rectangular or of other geometry.

The passive resonator circuit 13 of the present invention need not be encapsulated so that stimuli directly applied to the layer of solid dielectric material may be measured.

For clinical and other applications, a passive resonator circuit composed only of an unconnected pair of single component L-C elements sandwiching a solid dielectric layer is highly robust due to the absence of an electrical interconnector that may fail.

In one embodiment, each coil 20, 22 may comprise a wire 28 wound concentrically around itself from a central point outward. The wire 28 is wound continuously with only a thin insulator 30 between windings. In place of the wire, any conductor, whether flat, round or other shape in cross-section, can be used. The insulator 30 between windings can be air or any other dielectric material.

Each coil 20, 22 is, preferably, substantially flat and wound in a flat plane. In a preferred embodiment, an adhesive 32, such as an epoxy, is used to maintain the shape and orientation of the coiled wires so that they stay in an essentially flat configuration once wound. Of course, other materials can be used to maintain the shape of each coil including solid supporting materials or a stiff insulating jacket on the wires themselves. The sensor may further include a substrate to maintain the shape of the wound coil. The substrate may comprise an epoxy, a polymer, an elastomer, a ceramic or a composite material.

In the preferred embodiment, the coils are between 1 mm and 6 mm in diameter although smaller and larger diameter coils may be used. The thickness of the conductor is preferably between 0.05 mm and 0.25 mm although other thicknesses may be employed. In the preferred embodiment, the number of turns in a coil ranges from 25 to 250 although more or less turns may be used.

The Applicants have fabricated implantable sensors comprising flat inductor coils, which also advantageously serve as capacitive plates. The coils have been fabricated from 30, 34, 38, and 40 gauge copper magnet wire, although any conductive wire (including silver, gold, platinum, etc.) will work. The wires were hand wound into a coil around a mandrel using two glass slides to maintain the planar shape of the coil. See FIG. 6. M bond A E-15 epoxy (from Vishay Micromeasurement Group) was used to maintain the wire in the desired shape, although any slow curing epoxy or the equivalent may be used. The sample coils had a diameter of about 5 mm but larger or smaller coils may be employed.

Figure 6:
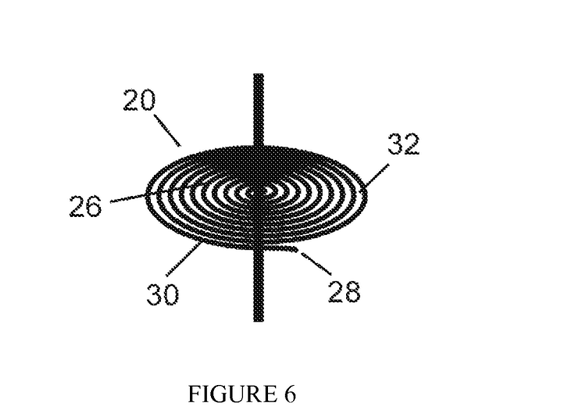
FIG. 6 depicts coil fabrication on a mandrel according to the present invention.

This mandrel-glass slide-coil assembly is placed in an oven to allow the epoxy to polymerize. The coils are then removed from the mandrel apparatus. The centers of each coil may then be filled with epoxy and allowed to polymerize.

Once individual coils are fabricated, they are then assembled into sensors. To fabricate sensors, pairs of coils, preferably, but not necessarily, oppositely wound, are aligned concentrically. The coils need not be concentrically aligned, but inductance is maximized when they are aligned. A biocompatible and hydrophobic dielectric is preferably applied between the two coils. Any dielectric can be used, but a biocompatible hydrophobic dielectric is optimal for implantable sensors.

Figure 5:
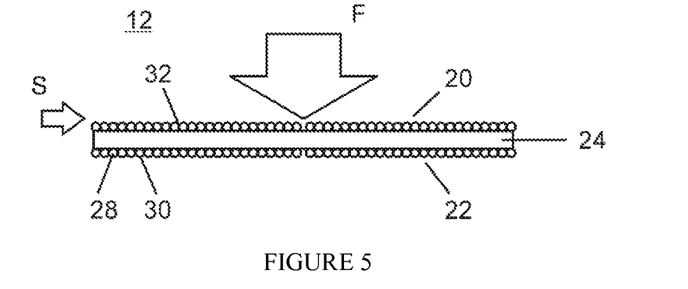
FIG. 5 is a cross-sectional view of an alternative un-bonded embodiment of the sensor of the present invention.

The dielectric can be applied as a liquid using a number of application techniques including manually dropping it onto one or both coils or spin coating one or both coils. The dielectric can also be applied as a solid by placing a thin sheet of polymer between the coils. For example, silicone conformal coatings, polyurethanes, and epoxies may be used as a dielectric. A dielectric of any layer thickness can be used, but layers in the range of 1-100 um are optimal. In certain applications, the solid dielectric may be porous. The coils are then assembled into pairs. The coils can either be bonded together using, for example, initially liquid dielectric (FIGS. 2-4) or they can remain as an unbound "stack" simply sandwiching the layer of solid dielectric material (FIG. 5). The properties of the sensors at low force are dictated by whether they are bound or not.

As an alternative, the sensors may be fabricated using micro machining and/or micro fabrication techniques including etching, deposition, micro machining, etc. Employing these standard techniques and available equipment, conductive coils sandwiching a dielectric can be fabricated with automated processes in batches, thus facilitating rapid and inexpensive fabrication of the sensors.

The sensor system of the present invention may be "tuned" to measure different stimuli by choosing a dielectric material having desired properties. A dielectric with high coefficient of thermal expansion will be sensitive to changes in temperature. A dielectric with very low stiffness (modulus of elasticity) would be sensitive to changes in force. A dielectric material such as a hydrogel which is sensitive to pH swells when pH changes. This swelling changes the spacing between the two coils resulting in a change in resonant frequency of the sensor. For each sensor, an appropriate dielectric is chosen based upon the physical parameter or other stimulus to be measured and those parameters to which the sensor should be insensitive.

The resonant frequency of the passive resonator circuit of the present invention is governed by the following relationships:

$$C = \frac{\in A}{l}. \qquad (1)$$

$$L_{coil} = \frac{r^2 N^2}{(2r + 2.8d) \times 10^5}. \qquad (2)$$

$$L_{Total} = L_{coil\,1} + L_{coil\,2} + 2M. \qquad (3)$$

$$f = \frac{1}{2\pi\sqrt{LC}}. \qquad (4)$$

Where C is capacitance, $\in$ is the emissivity, A is the area of only the conductor of the coil, l is the spacing between the coils, r is the mean coil radius, N is the number of turns in the coil, and d is the coil depth ($r_{outer}-r_{inner}$), $L_{Total}$ is the total circuit inductance, M is the mutual inductance between the coils, and f is the resonant frequency which is calculated from the system inductance (L) and capacitance (C).

Figure 8:
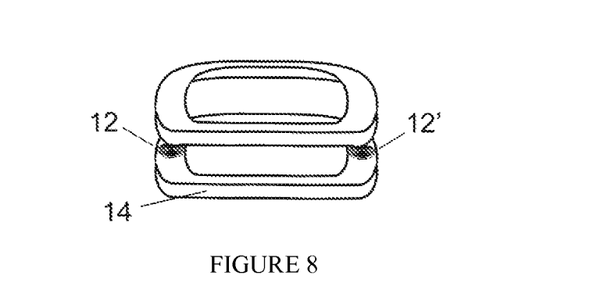
FIG. 8 depicts the sensor of the present invention attached to a smart implant.

For clinical applications, the sensor 12 of the present invention may be adapted to operate in an aqueous environment by encapsulating the conductor of each coil in a hydrophobic insulator, such as a polymer, elastomer, ceramic or composite. (parylene, PVC, Teflon or epoxy are currently preferred), and advantageously attached, by a biocompatible adhesive or otherwise, to a medical implant 14 to function as a "smart implant", as illustrated in FIG. 8. Due to its small size and simplicity, the sensor can advantageously be attached to the medical implant with little or no modification to the geometry of the medical implant. For other applications, the sensor may be attached to any support structure or be free-standing.

Figure 9:
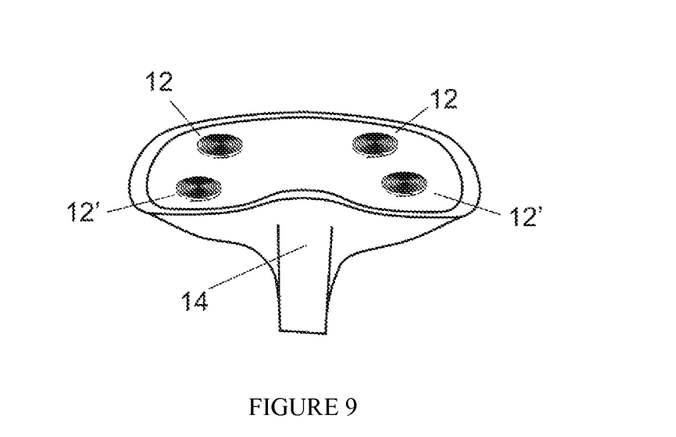
FIG. 9 depicts multiple sensors for multi-axial sensing of a stimulus and/or concurrent sensing of multiple stimuli.

As depicted in FIG. 9, multiple sensors, e.g. 12, 12', may be employed in a sensor system of the present invention for multi-axial sensing of a stimulus or concurrent sensing of multiple stimuli.

For resonant frequency measurements, a 75 ohm Agilent ENA L-RF Network Analyzer (E5062A) with a 75 ohm co-axial cable and a loop antenna was used to read the sample sensors. There are a number of antenna configurations that can be used to energize and read the sensors. These include flat coils, loops, spirals, etc. and combined multi-component arrays of these components. In one configuration, the Network Analyzer was set up to read channel S11, although a number of different Network Analyzers in different configurations could be used.

Figure 7:
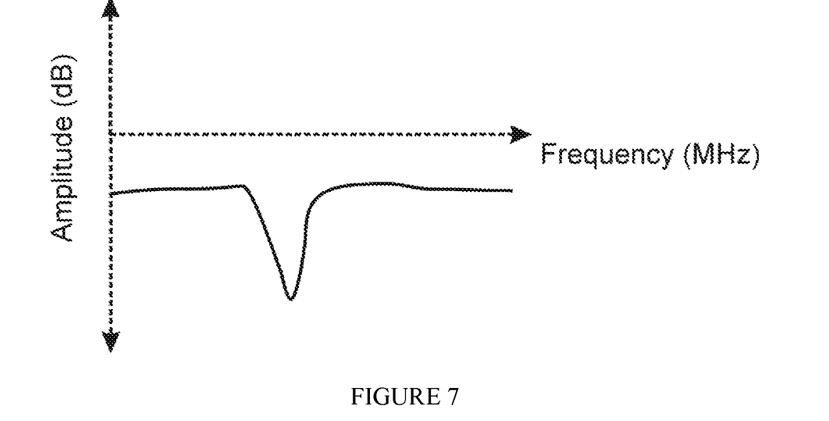
FIG. 7 is a graph depicting a dip associated with a sensed resonant frequency.

Displayed data were normalized to a stored background data set to enhance signal to noise ratio. The frequency sweep contained multiple points, e.g. about 100 points, usually over a 75 MHz range. For sensors of about 6 mm diameter fabricated from 38 gauge copper magnet wire, the resonant frequency ranges were from 25 to 125 MHz. The resonant frequency is visualized as a dip in a displayed S11 signal on the network analyzer, as illustrated in FIG. 7.

Figure 10:
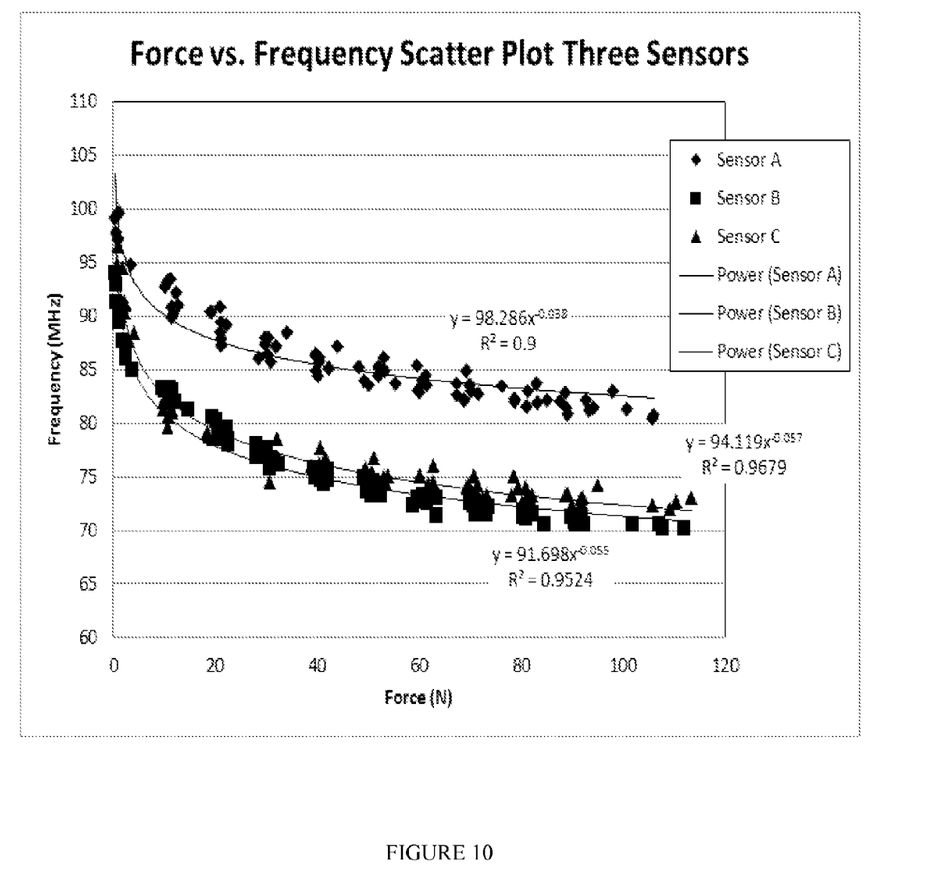
FIG. 10 is a graph of the frequency response to force, in air, under mechanical loading, of un-bonded sensors of the present invention.
Figure 11:
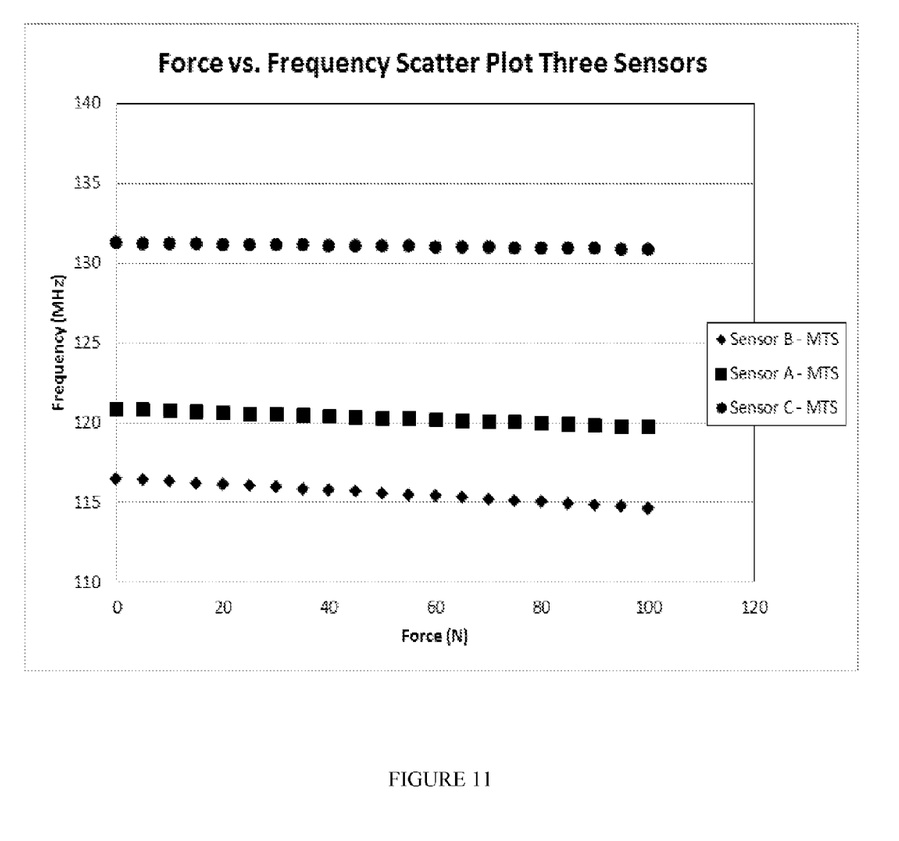
FIG. 11 is a graph of frequency response to force, in air, under mechanical loading, of bonded sensors of the present invention.

After fabrication, sensors were loaded in axial compression using a mechanical testing machine to characterize the response to force. Loading and unloading profiles were attained by loading sensors through various force ranges while simultaneously recording resonant frequency and displacement. In air, the changes in frequency decrease with increasing load, as illustrated in FIGS. 10 and 11. When the coils are not bonded to the layer of solid dielectric material, there is an initial non-linear toe-in region, as shown in FIG. 10. When the coils are bonded together on opposite sides of the dielectric layer, there is no toe-in region and the force-frequency relationship is generally linear, as shown in FIG. 11. Sensitivity of the sensor to load is dependent on several properties including the starting dielectric gap and the modulus of the dielectric, as shown by comparing FIGS. 10 and 11. The data were highly repeatable for each tested sensor.

FIG. 10 shows loading trials for three 6.5 mm diameter un-bonded sensors fabricated from 38 gauge wire. In air, under mechanical loading, the un-bonded sensors respond with decreasing frequency.

FIG. 11 shows loading trials for three 6.5 mm diameter bonded sensors fabricated from 38 gauge wire. In air, under mechanical loading, bonded (but electrically unconnected) sensors respond linearly with decreasing frequency.

Figure 12:
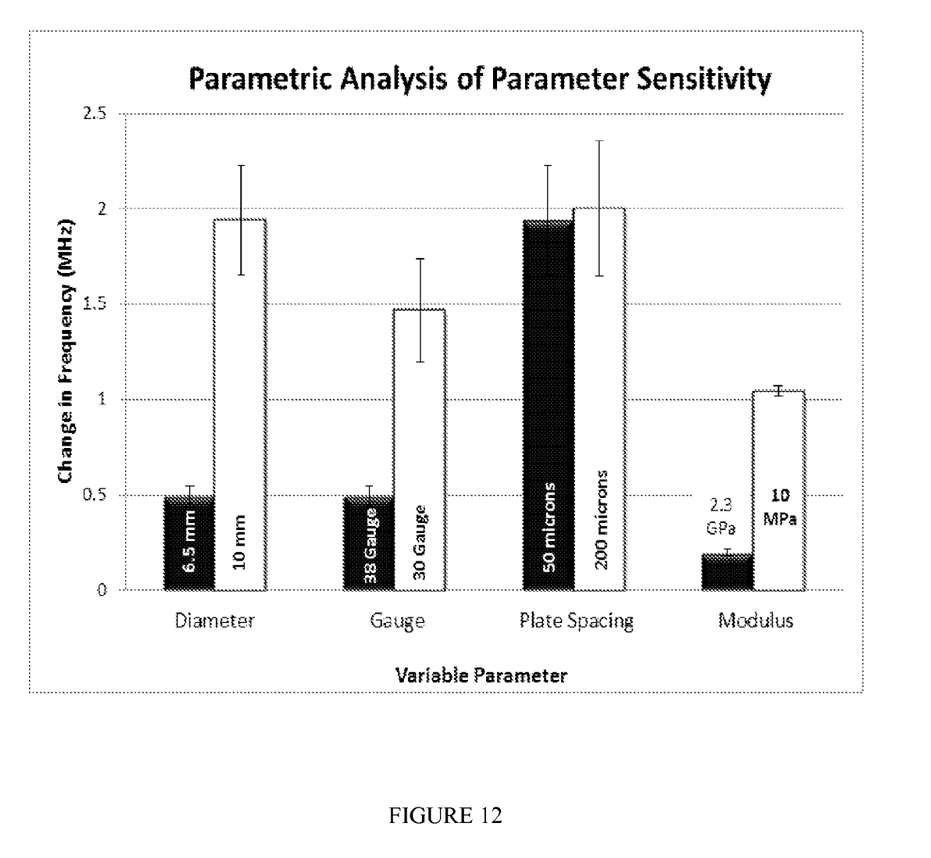
FIG. 12 is a bar graph presenting a parametric analysis of parameter sensitivity of the sensors of the present invention.
Figure 13:
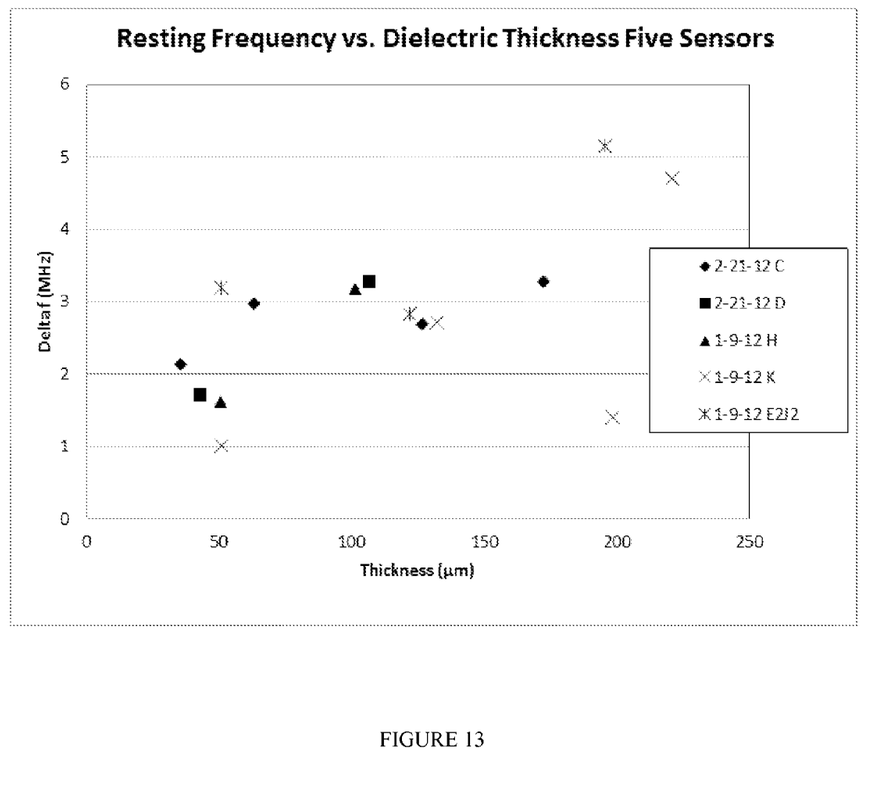
FIG. 13 is a graph of frequency change versus dielectric thickness for sensors of the present invention.
Figure 14:
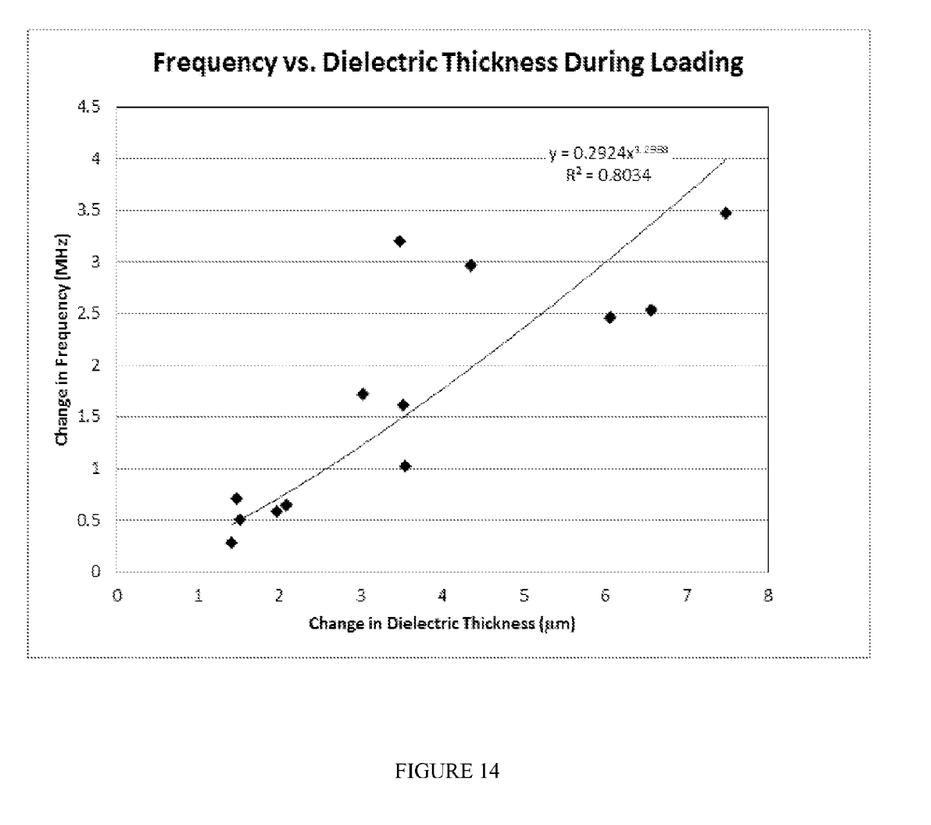
FIG. 14 is a graph of frequency change with variation in dielectric thickness.

The effects of coil diameter, wire gauge, coil spacing (dielectric thickness), and dielectric modulus have been characterized. As shown in FIGS. 12 and 13, small changes in coil spacing having only a subtle effect on sensor sensitivity relative to the substantial change from diameter, gauge and modulus. As expected, change in frequency correlates strongly to change in coil spacing (dielectric thickness) as shown in FIG. 14.

Figure 15:
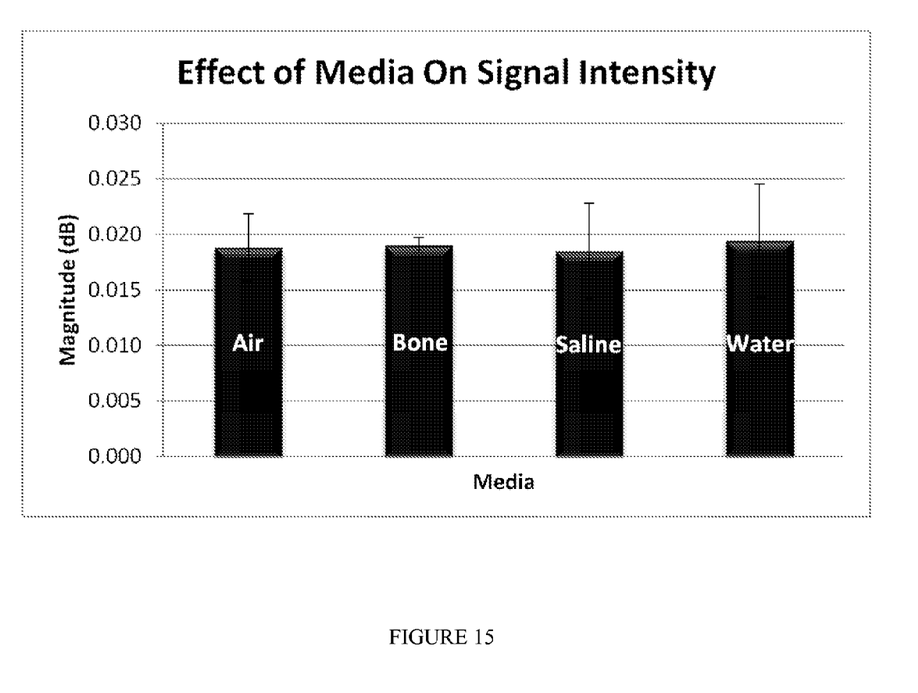
FIG. 15 is a bar graph indicating the effect of media on grid dip intensity.

Importantly, the intensity of the grid dip (energy absorption) by the sensor was not affected by introduction of water, saline, or up to 5 mm of cortical bone between the sensor and the antenna, as shown in FIG. 15. The introduction of bone did not affect the resonant frequency relative to measurements in air, but reading through water reduced the resonant frequency by 16.7% and reading through saline reduced the resonant frequency by 29.4%.

Figure 16:
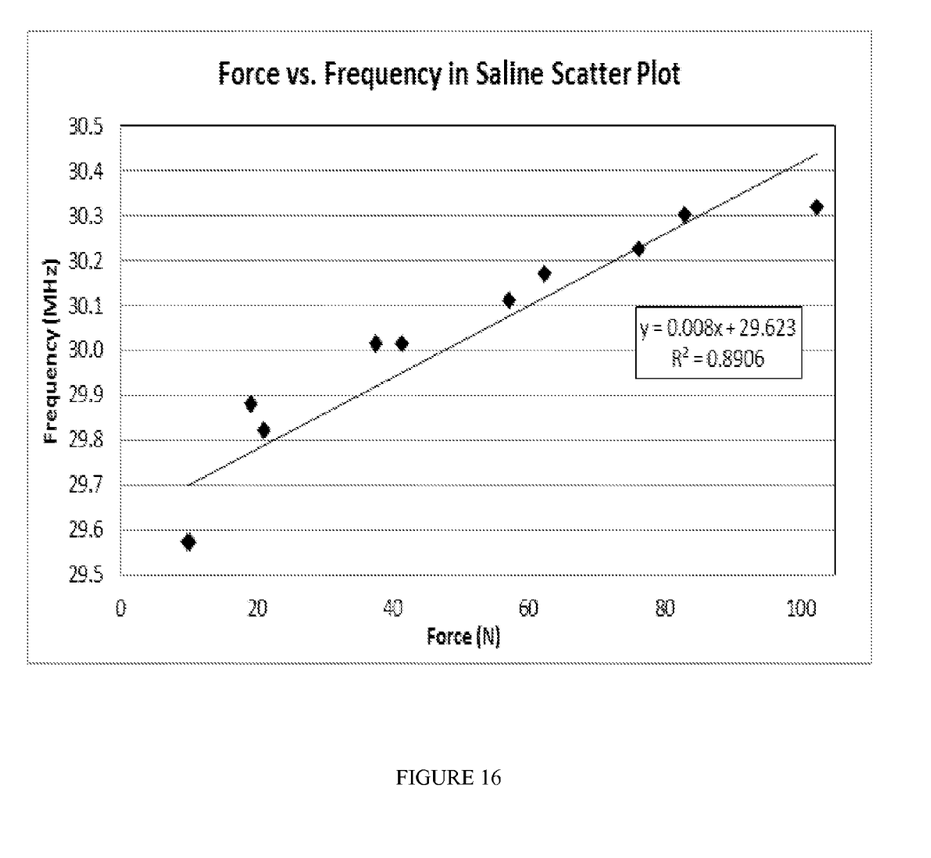
FIG. 16 is a graph of frequency versus force of a dielectric saturated in saline.

Immersion in saline does have one substantial and unpredicted effect on sensor performance. Once the dielectric reaches equilibrium with respect to moisture absorption, the response of the sensor to axial loading is substantially altered. Once the dielectric is saturated, axial load causes an increase in sensor frequency with increased loading, as shown in FIG. 16. The change in frequency is linear with respect to load. The response of the sensor in saline is dependent on the dielectric properties.

Figure 17:
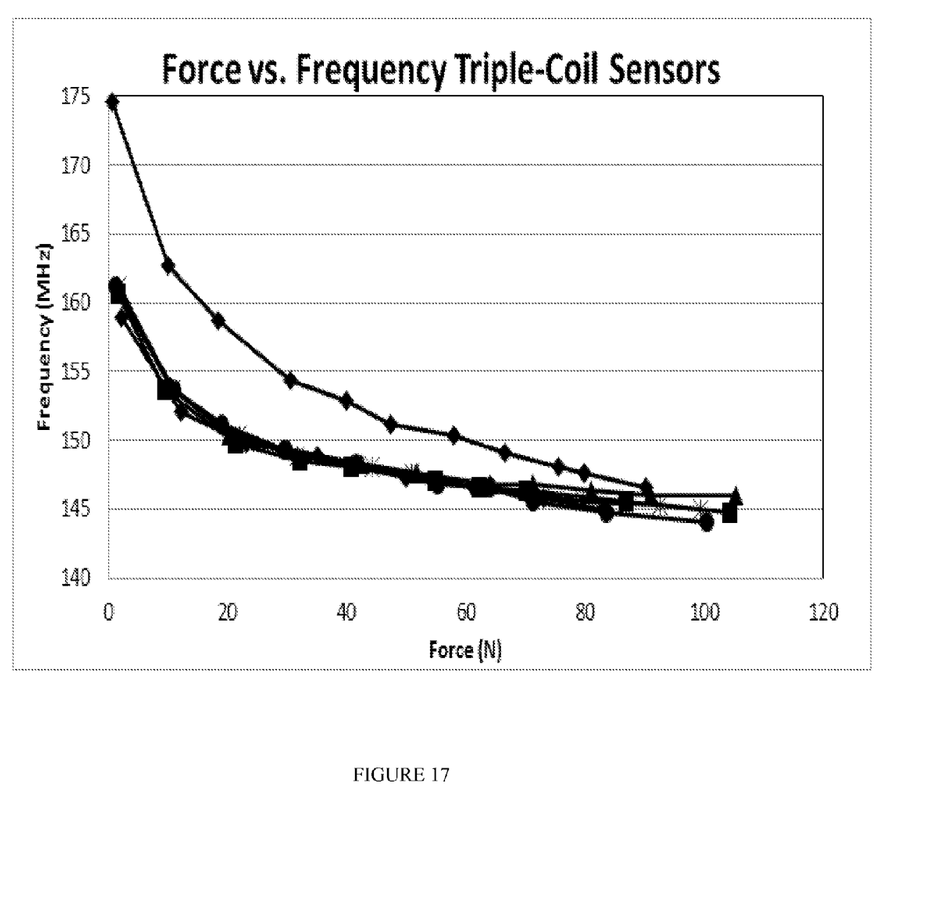
FIG. 17 is a graph of frequency versus force for a 3 coil configuration of the sensor of the present invention.

To increase the inductance and lower the resting resonant frequency of the sensor, additional spirally wound conductive coils with intervening layers of solid dielectric material can be added to the sensor. FIG. 17 illustrates the loading results of a sensor comprising a stack of three unconnected spiral coils with dielectric between each of the coil pairs. More than 3 coils may also be employed.

The present invention thus provides a wireless, batteryless and telemetryless sensor system employing a simplified passive resonator circuit with no electrical connections. With no electrical connections to fail, the sensors are robust.

They may be unenclosed and require no hermetic seal, are extremely inexpensive to fabricate and because of their very small size and simple construction, require little or no implant modification. Significantly, these implantable sensors enable daily clinical usage in smart implants. The use of such smart implants in personalized medicine will improve outcomes and reduce costs by enabling more accurate diagnoses and more optimal treatments. Patients with such smart implants will be back to health and back to work more quickly, thus reducing the impact on an individual's life and the overall economic burden of disease.

What is claimed is:

1. A method of sensing a stimulus in vivo, comprising:
   implanting in a patient, in a position subject to the stimulus, a passive resonator circuit with a characteristic resonant frequency and comprising at least a pair of generally parallel spirally wound unconnected conductive coils with a spacing in between, wherein the characteristic resonant frequency is defined by the spacing of the generally parallel spirally wound unconnected conductive coils, and further comprising a layer of solid dielectric material with at least one dimensional property and positioned in between the pair of generally parallel spirally wound unconnected conductive coils, wherein the layer of solid dielectric material is exposed to the stimulus in vivo, and the layer of solid dielectric material is configured to sense the stimulus via a variation in the at least one dimensional property, wherein such variation in the at least one dimensional property changes the characteristic resonant frequency of the passive resonator by altering the spacing between the pair of generally parallel spirally wound unconnected conductive coils;
   energizing the passive resonator circuit with radiofrequency energy from a source external to the patient; and
   remotely detecting a change in the characteristic resonant frequency of the energized passive resonator circuit, with a detector, wherein the detected change in the characteristic resonant frequency provides a measurement of the stimulus.

2. The method of claim 1, wherein the implanting comprises attaching the passive resonator circuit to a medical implant, and implanting the medical implant and the attached passive resonator circuit in the patient, and wherein each coil is encapsulated in insulating material and the layer of solid dielectric material is biocompatible and hydrophobic.

3. An implantable sensor for sensing a stimulus in vivo, comprising a passive resonator circuit with a characteristic resonant frequency and including at least a pair of generally parallel spirally wound unconnected conductive coils with a spacing in between, wherein the characteristic resonant frequency is defined by the spacing of the generally parallel spirally wound unconnected conductive coils, and further comprising a layer of solid dielectric material with a thickness and positioned in between the pair of generally parallel spirally wound unconnected conductive coils, wherein the layer of solid dielectric material is exposed to the stimulus, and the layer of solid dielectric material is configured to sense the stimulus via a variation in the thickness, wherein the variation in the thickness changes the characteristic resonant frequency of the passive resonator circuit by altering the spacing between the pair of generally parallel spirally wound unconnected conductive coils.

4. The sensor of claim 3, in combination with a medical implant, wherein the sensor is physically attached to the medical implant.

5. The sensor of claim 3, further comprising at least one additional said sensor providing multi-axial sensing of said stimulus and/or concurrent sensing of multiple stimuli.

6. The sensor of claim 3, wherein the stimulus comprises at least one of force, load, strain, shear, temperature, absolute pressure, displacement, pH, deformation, chemical marker and biomarker.

7. The sensor of claim 3, wherein the sensor is devoid of an enclosure.

8. The sensor of claim 7, wherein the passive resonator circuit is adapted to operate in an aqueous liquid environment.

9. The sensor of claim 8, wherein the passive resonator circuit is adapted to operate in the aqueous liquid environment by encapsulating a conductor of each coil in a hydrophobic insulator.

10. The sensor of claim 3, wherein the passive resonator circuit is adapted to be remotely energized, batteryless and telemetryless.

11. The sensor of claim 3, wherein a first coil of said pair is wound clockwise, and a second coil of said pair is wound counterclockwise.

12. The sensor of claim 11, wherein the first coil and the second coil are flat, substantially parallel to each other, and disposed on opposite surfaces of the solid dielectric layer.

13. The sensor of claim 12, wherein the first coil and the second coil adhere to respective opposite surfaces of the solid dielectric layer.

14. The sensor of claim 11, wherein the first coil and the second coil comprise insulated wires wound concentrically that maintain their respective shape after being wound.

15. The sensor of claim 14, wherein windings of each coil are bonded together to maintain their respective shape.

16. The sensor of claim 14, further including a substrate to maintain the shape of the wound coil.

17. The sensor of claim 16, wherein the substrate comprises at least one of an epoxy, a polymer, an elastomer, a ceramic, a composite material, and a rigid support material.

18. The sensor of claim 3, wherein each coil comprises a conductor wound concentrically and continuously around itself from a central point outward with an insulator between windings.

19. The sensor of claim 3, wherein at least one coil of the pair comprises a micro machined or micro fabricated part.

20. The sensor of claim 3, in operative combination with an energizer for energizing the passive resonator circuit with radiofrequency energy, and a detector for detecting a change in the characteristic resonant frequency of the passive resonator circuit to provide a measurement of the stimulus.

21. The sensor of claim 20, wherein the energizer and the detector comprise a grid dip oscillator and an antenna.

22. The sensor of claim 3, wherein the passive resonator circuit is composed of biocompatible material and adapted for implantation in a patient for sensing the stimulus in vivo.

23. The sensor of claim 3, wherein each coil is encapsulated in insulating material, and the layer of solid dielectric material is directly exposed to the stimulus.

24. A smart implant comprising a medical implant and an implantable sensor for sensing a stimulus in vivo, the implantable sensor being mounted to the medical implant and comprising a passive resonator circuit with a characteristic resonant frequency and including at least a pair of generally parallel spirally wound unconnected conductive coils with a spacing in between, wherein the characteristic resonant frequency is defined by the spacing of the generally parallel spirally wound unconnected conductive coils, and the passive resonator circuit further comprises a layer of solid dielectric material with a thickness and positioned in between the pair of generally parallel spirally wound unconnected conductive coils, wherein the layer of solid dielectric material is exposed to the stimulus, and the layer of solid dielectric material is configured to sense the stimulus via a variation in the thickness, wherein the variation in the thickness changes the characteristic resonant frequency of the passive resonator circuit by altering the spacing between the pair of generally parallel spirally wound unconnected conductive coils, and wherein the passive resonator circuit is composed of biocompatible material and adapted for implantation in a patient for sensing the stimulus in vivo.

25. A sensor system comprising:
a medical implant;
an implantable sensor for sensing a stimulus in vivo, the implantable sensor being mounted to the medical implant and comprising a passive resonator circuit with a characteristic resonant frequency and including at least a pair of generally parallel spirally wound unconnected conductive coils with a spacing in between, wherein the characteristic resonant frequency is defined by the spacing of the generally parallel spirally wound unconnected conductive coils, and the passive resonator circuit further comprises a layer of solid dielectric material with a thickness and positioned in between the pair of generally parallel spirally wound unconnected conductive coils, wherein the layer of solid dielectric material is exposed to the stimulus, and the layer of solid dielectric material is configured to sense the stimulus via a variation in the thickness, wherein the variation in the thickness changes the characteristic resonant frequency of the passive resonator circuit by altering the spacing between the pair of generally parallel spirally wound unconnected conductive coils, and wherein the passive resonator circuit is composed of biocompatible material and adapted for implantation in a patient for sensing the stimulus in vivo;
an energizer, external to the patient, for energizing the passive resonator circuit with radiofrequency energy; and
a detector, external to the patient, for detecting a change in the characteristic resonant frequency of the passive resonator circuit to provide a measurement of the stimulus.

26. A sensor for sensing a stimulus, comprising a passive resonator circuit with a characteristic resonant frequency and including at least a pair of generally parallel spirally wound unconnected conductive coils with a spacing in between, wherein each coil is encapsulated in insulating material, wherein the characteristic resonant frequency is defined by the spacing of the conductive coils, the passive resonator circuit further comprises a layer of solid dielectric material with a physical dimension, the layer of solid dielectric material being positioned in between the pair of generally parallel spirally wound unconnected conductive coils and exposed to the stimulus, and the layer of solid dielectric material is configured to sense the stimulus via a variation in the physical dimension, wherein the variation in the physical dimension changes the characteristic resonant frequency of the passive resonator circuit by altering the spacing between the pair of generally parallel spirally wound unconnected conductive coils.

27. The sensor of claim 26, wherein said stimulus comprises axial force and the physical dimension comprises an axial dimension of the solid dielectric layer, or the stimulus comprises strain and the physical dimension comprises surface displacement.

28. The sensor of claim 26, wherein the physical dimension of the layer of solid dielectric material changes in response to direct application of the stimulus to the layer, and the physical dimension comprises at least one of surface deformation, surface displacement, layer dimension, layer size, layer shape, and layer volume.

29. The sensor of claim 26, wherein the sensor is devoid of an enclosure and not hermetically sealed, and the solid dielectric material comprises a biocompatible material.

30. The sensor of claim 26, wherein the solid dielectric material comprises a hydrophobic material.

31. The sensor of claim 26, wherein the solid dielectric material comprises a biocompatible, hydrophobic material.

32. The sensor of claim 26, wherein the coils are between 1 mm and 6 mm in diameter.

33. The sensor of claim 26, wherein number of turns in each coil ranges from 25 to 250.

34. The sensor of claim 26, wherein each conductive coil includes a conductor having a thickness between 0.05 mm and 0.25 mm.

35. The sensor of claim 26, wherein the layer of solid dielectric material has a thickness in a range of 1-100 µm.

36. The sensor of claim 26, wherein: the coils are between 1 mm and 6 mm in diameter, number of turns in each coil ranges from 25 to 250, and the layer of solid dielectric material has a thickness in a range of 1-100 µm.

37. The sensor of claim 26, wherein the physical dimension of the layer of solid dielectric material varies in response to a particular stimulus, and is invariable in response to other stimuli.

38. The sensor of claim 37, wherein the particular stimulus comprises one of: a change in temperature, a change in force, and a change in pH.

39. The sensor of claim 26, wherein the stimulus comprises at least one of force, load, strain, shear, temperature, absolute pressure, displacement, pH, deformation, chemical marker and biomarker.

* * * * *